United States Patent [19]

Ondetti et al.

[11] 4,154,935
[45] May 15, 1979

[54] HALOGEN SUBSTITUTED MERCAPTOACYLAMINO ACIDS

[75] Inventors: Miguel A. Ondetti, Princeton; Peter W. Sprague, Pennington, both of N.J.

[73] Assignee: E. R. Squibb & Sons, Inc., Princeton, N.J.

[21] Appl. No.: 939,147

[22] Filed: Sep. 1, 1978

Related U.S. Application Data

[63] Continuation-in-part of Ser. No. 879,032, Feb. 21, 1978, abandoned.

[51] Int. Cl.$^2$ .......................................... C07D 211/60
[52] U.S. Cl. ..................................... 546/189; 260/326; 260/25; 260/326.2; 546/245; 424/267; 424/274
[58] Field of Search ........................ 260/293.63, 293.85

[56] References Cited

U.S. PATENT DOCUMENTS

| | | | |
|---|---|---|---|
| 4,046,889 | 9/1977 | Ondetti et al. | 260/239 AR |
| 4,052,511 | 10/1977 | Cushman et al. | 260/239 AR |
| 4,070,361 | 1/1978 | Petrillo | 260/293.85 |
| 4,086,338 | 4/1978 | Ondetti et al. | 260/239 AR |
| 4,091,024 | 5/1978 | Ondetti | 260/293.63 |
| 4,105,776 | 8/1978 | Ondetti et al. | 260/293.64 |

OTHER PUBLICATIONS

Shirota et al., "J. Med. Chem.", vol. 20, pp. 1176–1181, (1977).

*Primary Examiner*—Natalie Trousof
*Assistant Examiner*—Robert T. Bond
*Attorney, Agent, or Firm*—Lawrence S. Levinson; Merle J. Smith

[57] ABSTRACT

New halogen substituted mercaptoacylamino acids which have the general formula

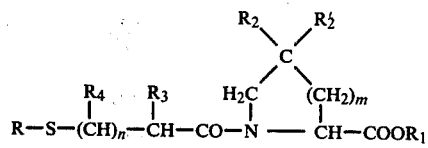

are useful as hypotensive agents.

18 Claims, No Drawings

HALOGEN SUBSTITUTED MERCAPTOACYLAMINO ACIDS

This application is a continuation-in-part of application Ser. No. 879,032, filed Feb. 21, 1978, now abandoned.

SUMMARY OF THE INVENTION

This invention relates to new halogenated compounds which have the general formula

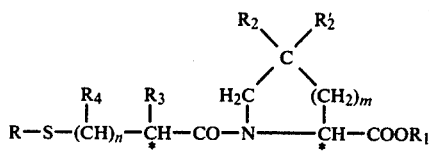

wherein R is hydrogen, lower alkanoyl or

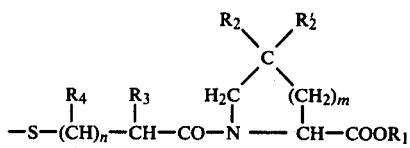

$R_1$ is hydrogen or lower alkyl;
$R_2$ and $R_2'$ each is hydrogen or halogen;
$R_3$ and $R_4$ each is hydrogen, lower alkyl or trifluoromethyl, not more than one being trifluoromethyl, and at least one of $R_2$, $R_2'$, $R_3$ or $R_4$ is a halogen or trifluoromethyl substituent represented by the named symbol as defined above;
m is 2; and
n is 0 or 1.

The asterisks indicate asymmetric carbon atoms.

DETAILED DESCRIPTION OF THE INVENTION

The invention in its broadest aspects as described in parent application Ser. No. 879,032 relates to halogenated derivatives of mercaptoacyl proline and mercapto acylpipecolic acids having formula I above. This application relates specifically to the pipecolic acids required to be divided from that parent application. The proline derivatives are described and claimed in an application filed concurrently herewith.

Preferred are those compounds of formula I wherein R is hydrogen or lower alkanoyl, especially hydrogen or acetyl; $R_1$ is hydrogen or lower alkyl, especially hydrogen; $R_2$ and $R_2'$ each is hydrogen or halogen especially hydrogen or fluorine; one of $R_3$ and $R_4$ is $CF_3$ and the other is hydrogen; m is 2 and n is 0 or 1, especially 1. $R_2$ and $R_2'$ can independently be hydrogen or halogen, but preferably both $R_2$ and $R_2'$ are the same, i.e., both are hydrogen or both are halogen, especially fluorine. When $R_3$ or $R_4$ is $CF_3$, both $R_2$ and $R_2'$ are preferably hydrogen.

The L-configuration for the proline or pipecolic acid is especially preferred.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The $C_1$–$C_4$ members, especially $C_1$ and $C_2$ members, are preferred.

The lower alkanoyl groups are those having the acyl radicals of the lower ($C_2$–$C_7$) fatty acids, for example, acetyl, propionyl, butyryl and the like. Similarly, those lower alkanoyl groups having up to four carbons, and especially acetyl, are preferred.

The halogens are the four common halogens, chlorine, bromine and fluorine being preferred, especially fluorine.

When n is 0 and $R_2$ and $R_2'$ are hydrogen, $R_3$ is trifluoromethyl. When n is 1 and $R_2$ and $R_2'$ are hydrogen either $R_3$ or $R_4$ is trifluoromethyl and the other is hydrogen. That is to say, either one or both of $R_2$ and $R'_2$ can be hydrogen or halogen and there is not more than one $CF_3$ group in the acyl side chain of the molecule. Also, if one or both of $R_2$ and $R_2'$ is halogen, $R_3$ and/or $R_4$ can be hydrogen or lower alkyl.

The products of formula I can be produced by various methods of synthesis.

In general, these compounds can be synthesized by coupling the acid of the formula

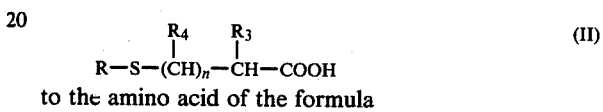

to the amino acid of the formula

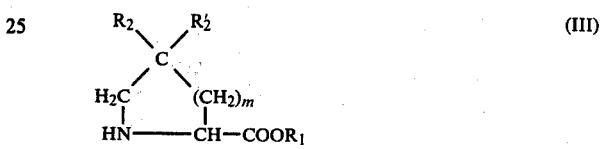

by any method which can be used to form amide bonds. See, for example, "Methoden der Organischen Chemie" (Houben-Weyl) part 1, p 736 et seq., part II, p 1 et seq. (1974).

The acids of formula II, when n is 1 can be obtained by the addition of a thioacid R-SH to 2-trifluoromethyl acrylic acid or 3-trifluoromethyl acrylic acid. The acids of formula II, when n is 0, are obtained by a displacement reaction using a thioacid R-SH and 2-halo-3,3,3-trifluoropropanoic acid.

According to one method, preferred when n is 0, an acid of formula III is coupled with a haloalkanoic acid of the formula

wherein X is halogen, preferably chlorine or bromine, by one of the known procedures in which the acid IV is activated, prior to reaction with the acid III, involving formation of a mixed anhydride, symmetrical anhydride, acid chloride, active ester, or use of Woodward reagent K, EEDQ (N-ethoxycarbonyl-2-ethoxy-1,2-dihydroquinoline) or the like.

The product of this reaction is a compound of the formula

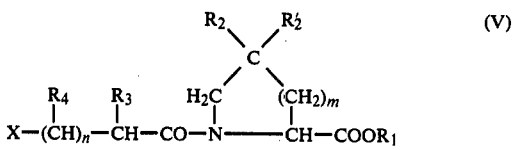

This product is subjected to a displacement reaction with the anion of a thioacid of the formula (VI) $R_5$—CO—SH wherein R₅ is lower alkyl yielding a product of the formula

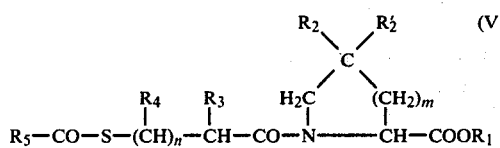

which can then be converted to the product

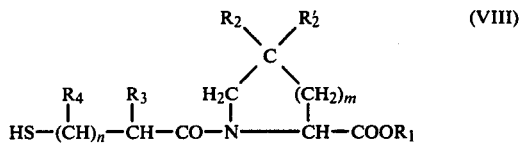

by ammonolysis. When R₁ is an ester group (i.e., R₁ is lower alkyl, obtained when an ester of the starting acid III is used), the ester group can be removed by conventional techniques. For example, when R₁ is tert-butyloxy or tert-amyloxy, treatment of the ester of formula VII or VIII with trifluoroacetic acid and anisole will give the corresponding free acid. When other alkoxy groups are present alkaline hydrolysis will yield the corresponding acid.

When an acid of formula III is used as starting material, or the final product is obtained as the free carboxylic acid, this acid can be converted to its ester, for example, by esterification with a diazoalkane, like diazomethane, 1-alkyl-b 3-p-tolyl-triazene, like 1-n-butyl-3-p-tolyltriazene or the like.

According to another variation, an ester preferably the methyl or t-butyl ester, of formula III, in an anhydrous medium such as dichloromethane, tetrahydrofuran, dioxane or the like, is treated with an acylthioalkanoic acid of the formula

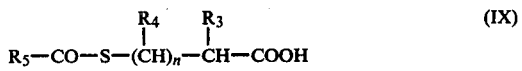

in the presence of dicyclohexylcarbodiimide, N,N'-carbonylbisimidazole, ethoxyacetylene, diphenylphosphoryl azide or similar coupling agent at a temperature in the range of about 0° to 10° C. The ester group can then be removed, for example, by treatment with trifluoroacetic acid and anisole at about room temperature to yield the free acid (R₁=H).

A variation, preferred when n is 1, R₄ is CF₃ and R₃ is H, is to react a thioacid of formula VI with an acrylic acid derivative of the formula

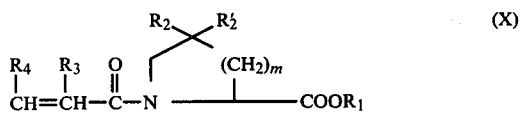

instead of with the compound of formula V, and then continue as described above. The compounds of formula X are obtained from 3-trifluoromethylacrylic acid and an ester of formula III by the method described in Example 18 below.

Compounds of formula I wherein R is

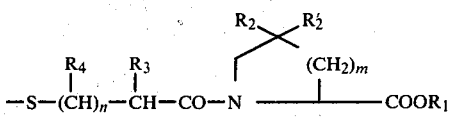

are produced by direct oxidation of a compound of formula I in which R is hydrogen, e.g., with iodine, to obtain the symmetrical bis compound.

Products of formula I have two asymmetric carbons. These carbon atoms are indicated by asterisks in formula I. The compounds accordingly exist in stereoisomeric forms or in racemix mixtures thereof. All of these are within the scope of the invention. The above described synthesis can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the cyclic amino acid constitutes the preferred isomeric form.

The compounds of this invention form basic salts with various inorganic and organic bases which are also within the scope of the invention. Such salts include ammonium salts, alkali metal salts with sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product.

The salts are formed in conventional manner by reacting the free acid form of the product with one or more equivalents of the appropriate base providing the desired salt ion, in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention are useful as hypotensive agents. They inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of compounds of formula I or physiologically acceptable salt thereof, angiotensin dependent hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or a mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention and constitute especially preferred embodiments. All temperatures are in degrees Celsius.

EXAMPLE 1

3-Acetylthio-2-trifluoromethylpropanoic acid

A mixture of thiolactic acid (50 g.) and 2-(trifluoromethyl)acrylic acid [M. W. Buxton, et al., J. Chem. Soc., 366 (1954)] (66 g.) is heated on the steam bath for one hour and then stored at room temperature for eighteen hours. The reaction mixture is distilled in vacuo to give 3-acetylthio-2-trifluoromethylpropanoic acid.

EXAMPLE 2

1-(3-Acetylthio-2-trifluoromethylpropanoyl)-L-proline tert-butyl ester

L-proline tert-butyl ester (5.1 g.) is dissolved in dichloromethane (40 mg.) and the solution is stirred and chilled in an ice bath. Dicyclohexylcarbodiimide (6.2 g.) dissolved in dichloromethane (15 ml.) is added followed immediately by a solution of 3-acetylthio-2-trifluoromethylpropanoic acid (6.5 g.) in dichloromethane (5 ml.). After fifteen minutes stirring in the ice bath and sixteen hours at room temperature, the precipitate formed is filtered off and the filtrate is concentrated to dryness in vacuo. The residue is dissolved in ethyl acetate and washed neutral. The organic phase is dried over magnesium sulfate and concentrated to dryness in vacuo to give 1-(3-acetylthio-2-trifluoromethylpropanoyl)-L-proline tert-butyl ester.

EXAMPLE 3

1-(3-Acetylthio-2-trifluoromethylpropanoyl)-L-proline 1-(3-Acetylthio-2-trifluoromethylpropanoyl)-L-proline tert-butyl ester (8 g.) is dissolved in a mixture of anisole (55 ml.) and trifluoroacetic acid (110 ml.). After one hour storage at room temperature the solvent is removed in vacuo and the residue is precipitated several times from ether-hexane to give 1-(3-acetylthio-2-trifluoromethylpropanoyl)-L-proline.

EXAMPLE 4

1-(3-Mercapto-2-trifluoromethylpropanoyl)-L-proline 1-(3-Acetylthio-2-trifluoromethylpropanoyl)-L-proline (4 g.) is dissolved in a mixture of water (8 ml.) and concentrated ammonia (8 ml.) under a blanket of nitrogen. After twenty-five minutes stirring at room temperature, the reaction mixture is chilled, acidified and extracted with ethyl acetate. The organic layer is concentrated to dryness in vacuo to yield 1-(3-mercapto-2-trifluoromethylpropanoyl)-L-proline.

EXAMPLE 5

2-Bromo-3,3,3-trifluoropropanoic acid 3,3,3-Trifluoroalanine (88 g.) is dissolved in a mixture of potassium bromide (250 g.) and 2.5 N sulfuric acid (1.240 ml.). The solution is chilled to 0° with an ice-salt bath and sodium nitrite (65.5 g.) is added in small portions over a one hour period with vigorous stirring. The reaction mixture is stirred in the cooling bath for another hour and then extracted with ether. The organic layer is washed with water, dried over magnesium sulfate and concentrated to dryness in vacuo to yield 2-bromo-3,3,3-trifluoropropanoic acid.

EXAMPLE 6

2-Bromo-3,3,3-trifluoropropanoic acid chloride

A solution of 2-bromo-3,3,3-trifluoropropanoic acid (5 g.) in thionyl chloride (5 ml.) is refluxed in the steam bath for two hours. The excess thionyl chloride is removed in vacuo, and the residue distilled under reduced pressure to yield 2-bromo-3,3,3-trifluoropropanoic acid chloride.

EXAMPLE 7

1-(2-Acetylthio-3,3,3-trifluoropropanoyl)-L-proline

To a solution of L-proline (5.75 g.) in 1 N sodium hydroxide (50 ml.), chilled in an ice-water bath, 2-bromo-3,3,3-trifluoropropanoic acid chloride (12 g.) is added and the mixture is vigorously stirred at room temperature for three hours. A solution of thiolacetic acid (4 ml.) and potassium carbonate (4.8 g.) in water (50 ml.) is added and the mixture is stirred at room temperature for sixteen hours. After extraction with ethyl acetate, the aqueous layer is acidified with concentrated hydrochloric acid and extracted again with ethyl acetate. This last organic phase is dried over magnesium sulfate and concentrated to dryness in vacuo. The residue is chromatographed on a silica gel column with a mixture of benzene-acetic acid (7:2) to yield 1-(2-acetylthio-3,3,3-trifluoropropanoyl)-L-proline.

EXAMPLE 8

1-(2-Mercapto-3,3,3-trifluoropropanoyl)-L-proline 1-(2-Acetylthio-3,3,3-trifluoropropanoyl)-L-proline (4 g.) is dissolved in a mixture of water (8 ml.) and concentrated ammonia (8 ml.) under a blanket of nitrogen. After thirty minutes at room temperature, the reaction mixture is acidified and extracted with ethyl acetate. The organic phase is dried over magnesium sulfate and concentrated to dryness in vacuo to yield 1-(2-mercapto-3,3,3-trifluoropropanoyl)-L-proline.

EXAMPLE 9

1-(3-Mercapto-2-trifluoromethylpropanoyl)-L-pipecolic acid

By substituting L-pipecolic acid tert-butyl ester for the L-proline tert-butyl ester in the procedure of Example 2, and submitting the product to the procedures of Examples 3 and 4, 1-(3-mercapto-2-trifluoromethylpropanoyl-L-pipecolic acid is obtained.

EXAMPLE 10

1-(2-Mercapto-3,3,3-trifluoropropanoyl)-L-pipecolic acid

By substituting L-pipecolic acid for the L-proline in the procedure of Example 7, and then submitting the product to the procedure of Example 8, 1-(2-mercapto-3,3,3-trifluoropropanoyl)-L-pipecolic acid is obtained.

EXAMPLE 11

1,1'-[Dithiobis-(2-trifluoromethyl-3-propanoyl)]-bis-L-proline 1-(3-Mercapto-2-trifluoromethylpropanoyl)-L-proline (1 g.) is dissolved in water adjusted to pH 7 with N sodium hydroxide. An ethanolic solution of iodine is added dropwise while maintaining the pH between 6 and 7 by careful addition of N sodium hydroxide. When a permanent yellow color is obtained, the addition of iodine is stopped and the color is discharged with sodium thiosulfate. The reaction mixture is acidified and extracted with ethyl acetate. The organic layer is dried over magnesium sulfate and concentrated to dryness to yield 1,1'-[dithiobis-(2-trifluoromethyl-2-propanoyl)]-bis-L-proline.

EXAMPLE 12

1-(3-Acetylthio-2-trifluoromethylpropanoyl)-L-proline sodium salt

A suspension of 1-(3-acetylthio-2-trifluoromethylpropanoyl)-L-proline (1 g.) in water (10 ml.) is adjusted to pH 8 by addition of normal sodium hydroxide. The resulting solution is freeze dried to yield 1-(3-acetylthio-2-trifluoromethylpropanoyl)-L-proline sodium salt.

EXAMPLE 13

1-(3-Acetylthio-2-trifloromethylpropanoyl)-4,4-difluoro-L-proline

To a solution of 4,4-difluoro-2-proline (7.5 g.) in N sodium hydroxide (50 ml.) chilled in an ice-water bath, 3-acetylthio-2-trifluoromethylpropanoic acid chloride prepared from 3-acetylthio-2-trifluoromethylpropanoic acid and thionyl chloride by the procedure of Example 6, 12 g. is added and the mixture is vigorously stirred at room temperature for two hours. After acidification with concentrated hydrochloric acid, the aqueous mixture is extracted with ethyl acetate. The organic phase is dried over magnesium sulfate and concentrated to dryness to yield 1-(3-acetylthio-2-trifluoromethylpropanoyl)-4,4-difluoro-L-proline.

EXAMPLE 14

1-(3-Mercapto-2-trifloromethylpropanoyl)-4,4-difluoro-L-proline

By substituting 1-(3-acetylthio-2-trifluoromethylpropanoyl)-4,4-difluoro-L-proline for the 1-(3-acetylthio-2-trifluoromethylpropanoyl)-L-proline in the procedure of Example 4, 1-(3-mercapto-2-trifluoromethylpropanoyl)-4,4-difluoro-L-proline is obtained.

EXAMPLE 15

1-(3-Mercapto-2-trifluoromethylpropanoyl)-5,5-difluoro-DL-pipecolic acid

By substituting 5,5-difluoro-DL-pipecolic acid [obtained from 5-keto-DL-pipecolic acid by the procedure described in J. Med. Chem. 20, 1176 (1977)] for the 4,4-difluoro-L-proline in the procedure of Example 13 and submitting the product to the procedure of Example 14, 1-(3-mercapto-2-trifluoromethylpropanoyl)-5,5-difluoro-DL-pipecolic acid is obtained.

EXAMPLE 16

1,1'-[Dithiobis-(2-trifluoromethyl-3-propanoyl)]-bis-4,4-difluoro-L-proline

By substituting 1-(3-mercapto-2-trifluoromethylpropanoyl)-4,4-difluoro-L-proline for the 1-(3-mercapto-2-trifluoromethylpropanoyl)-L-proline in the procedure of Example 11, 1,1-[dithiobis-(2-trifluoromethyl-3-propanoyl)]-bis-4,4-difluoro-L-proline is obtained.

EXAMPLE 17

1,1'-[Dithiobis-(2-trifluoromethyl-3-propanoyl)]bis-5,5-difluoro-DL-pipecolic acid By substituting 1-(3-mercapto-2-trifluoromethylpropanoyl)-5,5-difluoro-DL-pipecolic acid for the 1-(3-mercapto-2-trifluoromethylpropanoyl)-L-proline in the procedure of Example 11, 1,1'-[dithiobis-(2-trifluoromethyl-3-propanoyl)]bis-5,5-difluoro-DL-pipecolic acid is obtained.

EXAMPLE 18

1-(4,4,4-Trifluoro-2-butenoyl)-L-proline

Boric anhydride (7.0 g., 0.1 mole) prepared by fusing boric acid in a platinum crucible and crushing under nitrogen is combined with ethyl 3-hydroxy-4,4,4-trifluorobutanoate (32.3 g., 0.173 mole) in a 50 ml. flask equipped with a Dean-Stark trap and the mixture is heated at 180° with a salt bath until all of the anhydride dissolves (6 hours). The heat is increased to 350° during which time 23 ml. of distillate accumulates in the trap. The distillate is returned to the reaction flask and the heating step is repeated. This process is repeated 4 times to assure complete dehydration of the hydroxy ester. The distillate is dissolved in petroleum ether, dried over phosphorus pentoxide and distilled, yielding 10 g. of 4,4,4-trifluoro-2-butenoic acid ethyl ester (b.p. 115°-120°) and 650 mg. of 4,4,4-trifluoro-2-butenoic acid (b.p. 150°, m.p. 53°-55° recrystallization from pentane).

The ester is combined with 10% aqueous sodium hydroxide (24 ml.) and stirred at 25° for 6 hours. The mixture is diluted with water and extracted with methylene chloride to remove unchanged material. The aqueous layer is adjusted to pH 3 with concentrated hydrochloric acid and this mixture is extracted with methylene chloride (3×50 ml.). The organic layers are combined, dried over sodium sulfate, concentrated and the residue distilled giving crystalline 4,4,4-trifluoro-2-butenoic acid (b.p. 145°-153°). Recrystallized from pentane, the acid melts at 54°-55°, yield 4.6 g.

A mixture of the 4,4,4-trifluoro-2-butenoic acid (4.91 g., 35 mmole), hydroxybenzotriazole (4.73 g., 35 mmole), L-proline-t-butyl ester (6.00 g., 35 mmole) and dicyclohexylcarbodiimide (7.22 g., 35 mmole) in methylene chloride (200 ml.) is stirred under nitrogen overnight at room temperature. The mixture is filtered, the filtrate washed with 5% sodium bisulfate (2×50 ml.) and saturated sodium bicarbonate (2×50 ml.), dried over sodium sulfate and concentrated to yield an oil. This is dissolved in ether and the solution is chilled and filtered free of precipitate. The filtrate is concentrated, yielding a solid (m.p. 95°–100°, 8.7 g.) which shows a single spot by TLC (silica gel EM 50/50, EtOAc/CH$_2$Cl$_2$, Rf=0.85).

A mixture of the above obtained 1-(4,4,4-trifluoro-2-butenoyl)-L-proline t-butyl ester (4.0 g., 13.6 mmole) is mixed with trifluoroacetic acid (60 ml.) and anisole (13 ml.) and stirred under nitrogen for one hour. The solvents are removed under vacuum and the residue, dissolved in ether (10 ml.), is poured into pentane (500 ml.). This precipitation technique is repeated and the residue allowed to stand at 0° for 72 hours during which time crystallization occurs. The 1-(4,4,4-trifluoro-2-butenoyl)-L-proline is recrystallized from ethyl acetate-hexane; yield 2.48 g., m.p. 119°–120°.

EXAMPLE 19

1-(3-Mercapto-4,4,4-trifluorobutanoyl)-L-proline

Thiolacetic acid (1.5 ml.) is combined with 1-(4,4,4-trifluoro-2-butenoyl)-L-proline (720 mg., 3 mmole) under argon and the mixture stirred at room temperature overnight. The excess thiolacetic acid is removed under vacuum and the residual 1-(3-acetylthio-4,4,4-trifluorobutanoyl)-L-proline is mixed with aqueous ammonia (15 ml. conc. NH$_3$+15 ml. water) and stirred for 2 hours at room temperature. The mixture is then diluted with ice and acidified with concentrated hydrochloric acid. The acid mixture is extracted with methylene chloride (3×50 ml.), The extracts dried over sodium sulfate and concentrated to yield an oil. This is purified by dissolving in water (double distilled), treating the solution with carbon and filtering through a millipore filter (0.4 m followed by 0.08 m). Lyophilization of this solution gives 700 mg. of 1-(3-mercapto-4,4,4-trifluorobutanoyl)-L-proline as a colorless glass. R$_f$(benzene: acetic acid 7:1) 0.24.

EXAMPLE 20

1-(3-Mercapto-4,4,4-trifluorobutanoyl)-L-pipecolic acid

By substituting L-pipecolic acid tert.-butyl ester for the L-proline tert.-butyl ester in the procedure of Example 18, and then submitting the product to the procedure of Example 19, 1-(3-mercapto-4,4,4-trifluorobutanoyl)-L-pipecolic acid is obtained.

EXAMPLE 21

3-Acetylthio-4,4,4-trifluorobutanoic acid chloride

By substituting 4,4,4-trifluoro-2-butenoic acid for the 2-trifluoromethyl acrylic acid in the procedure of Example 1, 3-acetylthio-4,4,4-trifluorobutanoic acid is obtained, then chlorinating with thionyl chloride as in Example 6, 3-acetylthio-4,4,4-trifluorobutanoic acid chloride is obtained.

EXAMPLE 22

1-(3-Mercapto-4,4,4-trifluorobutanoyl)-4,4-difluoro-L-proline

By substituting 1-(3-acetylthio-4,4,4-trifluorobutanoic acid chloride for the 3-acetylthio-2-trifluoromethylpropanoic acid chloride in the procedure of Example 13 and then submitting the product to the procedure of Example 4, 1-(3-mercapto-4,4,4-trifluorobutanoyl)-4,4,4-difluoro-L-proline is obtained.

EXAMPLE 23

1,1'-[Dithiobis-(4,4,4-trifluoro-3-butanoyl)]-bis-L-proline

By substituting 1-(3-mercapto-4,4,4-trifluorobutanoyl)-L-proline for the 1-(3-mercapto-2-trifluoromethylpropanoyl)-L-proline in the procedure of Example 11, 1,1'-[dithiobis-(4,4,4-trifluoro-3-butanoyl)]-bis-L-proline is obtained.

EXAMPLE 24

1-(3-Mercapto-2-trifluoromethylpropanoyl)-5,5-dichloro-DL-pipecolic acid

By substituting 5,5-dichloro-DL-pipecolic acid [prepared from 5-keto-DL-pipecolic acid and phosphorus pentachloride by a procedure similar to that described in J. Med. Chem. 20, 1176 (1977)] for the 4,4-difluoro-L-proline in the procedure of Example 13 and then submitting the product to the procedure of Example 14, 1-(3-mercapto-2-trifluoromethylpropanoyl)-5,5-dichloro-DL-pipecolic acid is obtained.

EXAMPLE 25

1-(3-Mercapto-2-methylpropanoyl)-5,5-difluoro-DL-pipecolic acid

By substituting 3-acetylthio-2-methylpropanoic acid chloride for the 3-acetylthio-2-trifluoromethylpropanoic acid chloride in the procedure of Example 13 and then submitting the product to the procedure of Example 14, 1-(3-mercapto-2-methylpropanoyl)-5,5-difluoro-DL-pipecolic acid is obtained.

EXAMPLE 26

1-(3-Mercapto-2-methylpropanoyl)-5-fluoro-DL-pipecolic acid

By substituting 3-acetylthio-2-methylpropanoic acid chloride for the 3-acetylthio-2-trifloromethylpropanoic acid chloride and 5-fluoro-DL-pipecolic acid [prepared from 5-hydroxypipecolic acid by a procedure similar to that described in Biochemistry, 4, 2507 (1965)] for the 4,4-difluoro-L-proline in the procedure of Example 13, and then submitting the product of the procedure of Example 14, 1-(3-acetylthio-2-methylpropanoyl)-5-fluoro-DL-pipecolic acid and 1-(3-mercapto-2-methylpropanoyl)-5-fluoro-DL-pipecolic acid are obtained.

EXAMPLE 27

1-(3-Mercaptopropanoyl)-5-bromo-DL-pipecolic acid

By substituting 3-acetylthiopropanoyl chloride for the 3-acetylthio-2-trifluoromethylpropanoic acid chloride and 5-bromo-DL-pipecolic acid [prepared from 5-hydroxypipecolic acid by a procedure similar to that described in *Aust. J. Chem.*, 20, 1943 (1967)] for 4,4-difluoro-L-proline in the procedure of Example 13 and submitting the product to the procedure of Example 14, 1-(3-acetylthiopropanoyl)-5-bromo-DL-pipecolic acid and 1-(3-mercaptopropanoyl)-5-bromo-DL-pipecolic acid are obtained.

EXAMPLE 28

1-(3-Acetylthio-2-trifluoromethylpropanoyl)-DL-pipecolic acid methyl ester

By substituting DL-pipecolic acid methyl ester for the L-proline tert-butyl ester in the procedure of Example 2, 1-(3-acetylthio-2-trifluoromethylpropanoyl)-DL-pipecolic acid methyl ester is obtained.

EXAMPLE 29

1-(3-Mercapto-2-trifluoromethylpropanoyl-DL-pipecolic acid methyl ester

By substituting DL-pipecolic acid methyl ester for the L-proline tert-butyl ester and 3-mercapto-2-trifluoromethyl propanoic acid for the 3-acetylthio-2-methylpropanoic acid in the procedure of Example 2, 1-(3-mercapto-2-trifluoromethylpropanoyl)-DL-pipecolic acid methyl ester is obtained.

EXAMPLE 30

1-(3-Propanoylthio-2-trifluoromethylpropanoyl)-5-fluoro-DL-pipecolic acid

By substituting thiopropanoic acid for the thiolacetic acid in the procedure of Example 1, and then submitting the product to the procedure of Example 26, 1-(3-propanoylthio-2-trifluoromethylpropanoyl)-5-fluoro-DL-pipecolic acid is obtained.

EXAMPLE 31

1-(3-Mercapto-2-methylpropanoyl)-5-fluoro-DL-pipecolic acid sodium salt

An aqueous solution of 1-(3-mercapto-2-methylpropanoyl)-5-fluoro-DL-pipecolic acid is mixed with an equimolar amount of aqueous N-sodium hydroxide and the solution is freeze dried.

EXAMPLE 32

1-(3-Mercaptopropanoyl)-5,5-dichloro-DL-pipecolic acid

By substituting 3-acetylthiopropanoic acid chloride for the 3-acetylthio-2-trifluoromethylpropanoic acid chloride in the procedure of Example 24, 1-(3-mercaptopropanoyl)-5,5-dichloro-DL-pipecolic acid is obtained.

What is claimed is:

1. A compound of the formula

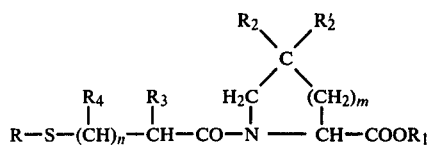

wherein R is hydrogen, lower alkanoyl or

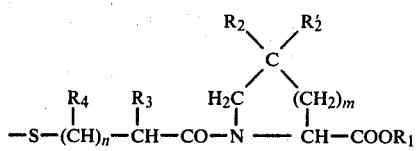

m is 2;
n is 0 or 1;
$R_1$ is hydrogen or lower alkyl;
$R_2$ and $R_2'$ each is hydrogen or halogen;
$R_3$ and $R_4$ each is hydrogen, lower alkyl or trifluoromethyl, not more than one being trifluoromethyl, and at least one of $R_2$, $R_2'$, $R_3$ or $R_4$ is a halogen or trifluoromethyl substituent represented by the named symbol as defined above; and basic salts thereof.

2. A compound as in claim 1 wherein n is 0 or 1; R is hydrogen or lower alkanoyl; $R_1$ is hydrogen or lower alkyl; $R_2$ and $R_2'$ is hydrogen or halogen; $R_3$ is trifluoromethyl when n is 0, either $R_3$ or $R_4$ is trifluoromethyl and the other is hydrogen when n is 1.

3. A compound as in claim 1 wherein R, $R_2$, $R_2'$ and $R_4$ all are hydrogen and $R_3$ is trifluoromethyl.

4. A compound as in claim 1 wherein R, $R_2$, $R_2'$ and $R_3$ all are hydrogen and $R_4$ is trifluoromethyl.

5. A compound as in claim 1 wherein $R_2$ is halogen and $R_2'$ is hydrogen.

6. A compound as in claim 5 wherein the halogen is fluorine.

7. A compound as in claim 1 wherein R is hydrogen and $R_2$ and $R_2'$ each is halogen.

8. A compound as in claim 7 wherein the halogen is fluorine.

9. A compound as in claim 1 wherein $R_1$ is hydrogen and n is 1.

10. A compound as in claim 1 wherein R and $R_1$ each is hydrogen, $R_2$ and $R_2'$ each is fluorine and n is 1.

11. A compound as in claim 1 wherein R, $R_1$, $R_2$ and $R_2'$ each is hydrogen, $R_3$ is trifluoromethyl and n is 0.

12. A compound as in claim 1 wherein R, $R_1$, $R_2$, $R_2'$ and $R_4$ each is hydrogen, $R_3$ is trifluoromethyl and n is 1.

13. A compound as in claim 1 wherein R, $R_1$, $R_2$ and $R_2'$ each is hydrogen, $R_3$ is trifluoromethyl and n is 0.

14. A compound as in claim 1 wherein R, $R_1$, $R_2$, $R_2'$ and $R_3$ each is hydrogen, $R_4$ is trifluoromethyl and n is 1.

15. A compound as in claim 1 wherein R is

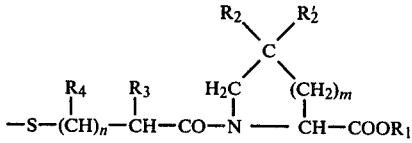

16. A compound as in claim 1 wherein R, $R_1$ and $R_4$ each is hydrogen, $R_2$ and $R_2'$ each is fluorine, $R_3$ is trifluoromethyl and n is 1.

17. A compound as in claim 15 wherein each $R_1$ and $R_4$ is hydrogen; each $R_2$ and $R_2'$ is fluorine, each $R_3$ is trifluoromethyl, and each n is 1.

18. A compound as in claim 1 wherein R, $R_1$ and $R_2$ each is hydrogen; $R_2'$ is fluorine; $R_3$ is methyl; $R_4$ is hydrogen and n is 1.

* * * * *